(12) United States Patent
Bossi et al.

(10) Patent No.: US 7,771,991 B2
(45) Date of Patent: Aug. 10, 2010

(54) CELL CULTIVATING FLASK

(75) Inventors: Stephen R. Bossi, Bedford, MA (US); Kathy M. Youngbear, Cambridge, MA (US)

(73) Assignee: Corning Incorporated, Corning, NY (US)

( * ) Notice: Subject to any disclaimer, the term of this patent is extended or adjusted under 35 U.S.C. 154(b) by 993 days.

(21) Appl. No.: 11/375,157

(22) Filed: Mar. 13, 2006

(65) Prior Publication Data
US 2006/0205065 A1    Sep. 14, 2006

Related U.S. Application Data

(60) Provisional application No. 60/662,039, filed on Mar. 14, 2005.

(51) Int. Cl.
C12M 1/24    (2006.01)
C12M 3/00    (2006.01)

(52) U.S. Cl. .................. 435/304.1; 435/304.3

(58) Field of Classification Search ... 435/304.1–304.3, 435/288.1, 288.5, 297.5, 305.3
See application file for complete search history.

(56) References Cited

U.S. PATENT DOCUMENTS

| | | | | |
|---|---|---|---|---|
| 3,071,271 A | * | 1/1963 | Thomas ..................... 215/224 |
| 3,870,602 A | * | 3/1975 | Froman et al. ........... 435/304.3 |
| 4,493,427 A | * | 1/1985 | Wolkonsky ................. 215/230 |
| D285,725 S | * | 9/1986 | Franchere ................. D24/224 |
| 5,100,009 A | * | 3/1992 | Thompson et al. .......... 215/341 |
| 5,272,084 A | * | 12/1993 | O'Connell et al. .......... 435/395 |
| 5,428,980 A | * | 7/1995 | Iidaka ........................... 72/83 |
| 5,565,353 A | | 10/1996 | Klebe et al. ............ 435/240.25 |
| 5,924,583 A | * | 7/1999 | Stevens et al. ................ 215/40 |
| 6,063,618 A | * | 5/2000 | Weuster-Botz et al. ... 435/294.1 |
| 6,114,165 A | | 9/2000 | Cai et al. ................. 435/304.3 |
| 6,569,675 B2 | * | 5/2003 | Wall et al. ................ 435/304.2 |
| 7,078,228 B2 | * | 7/2006 | Lacey et al. ............. 435/288.1 |
| 2005/0148068 A1 | * | 7/2005 | Lacey et al. ............. 435/297.5 |

FOREIGN PATENT DOCUMENTS

EP    0141104    *    8/1984

* cited by examiner

*Primary Examiner*—Walter D Griffin
*Assistant Examiner*—Shanta G Doe
(74) *Attorney, Agent, or Firm*—Susan S. Wilks; Thomas R. Beall

(57) ABSTRACT

A stackable flask for the culturing of cells is disclosed. The cell culture chamber is defined by a top plate and a rigid bottom tray of substantially rectangular shape connected by side and end walls, the body of the flask has imparted therein an opening connected to an angled neck, the neck being hydrophobic to keep fluid out. The neck is also modified to accept a snap-fit cap with a modified stepped skirt. The stepped skirt further prevents contamination by protecting the inner mating surface from contacting a surface. The size of the flask and location of an optional separate neck and cap section allows for flask manipulation by standard automated assay equipment, making the flask ideal for high throughput applications.

1 Claim, 12 Drawing Sheets

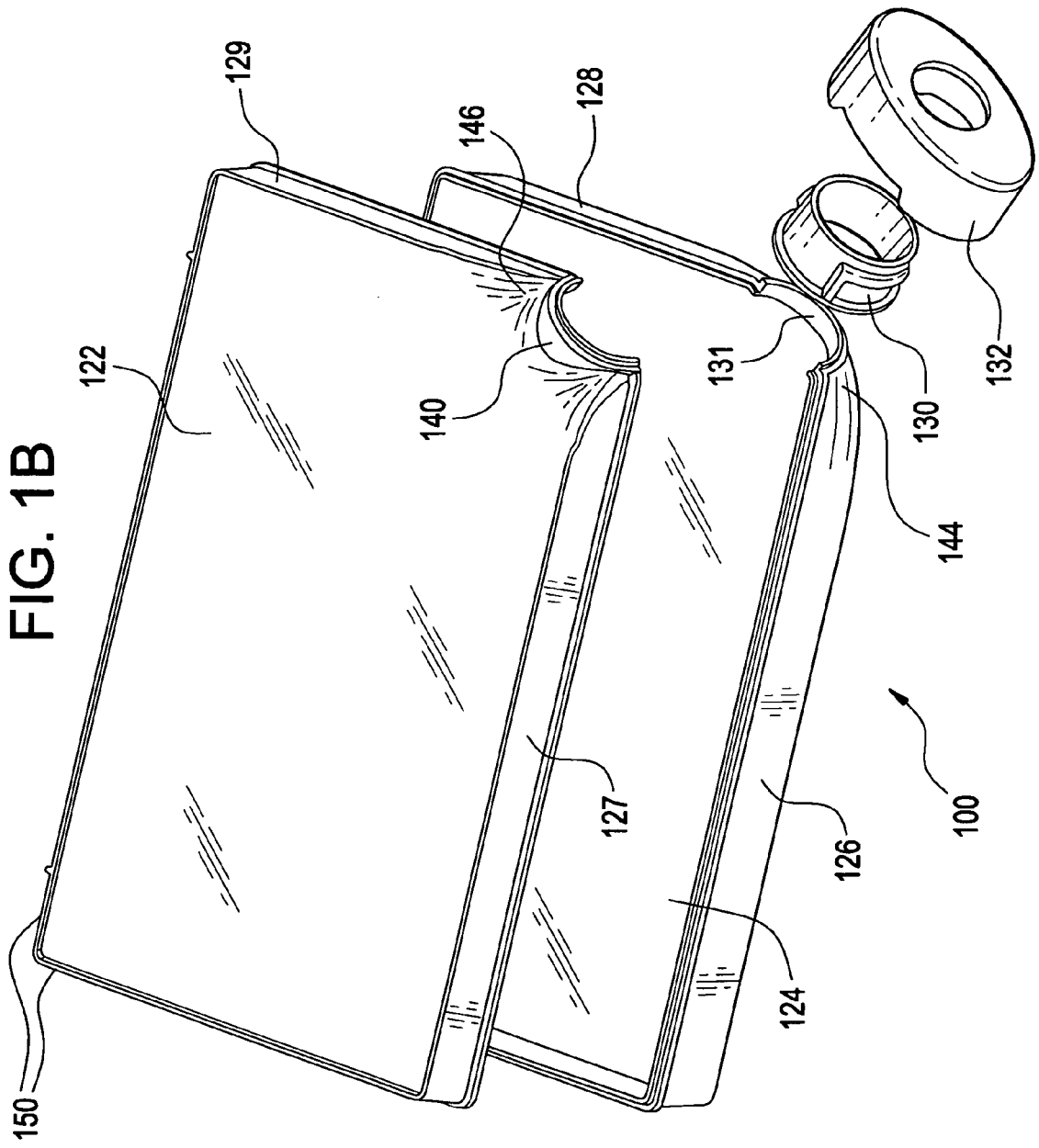

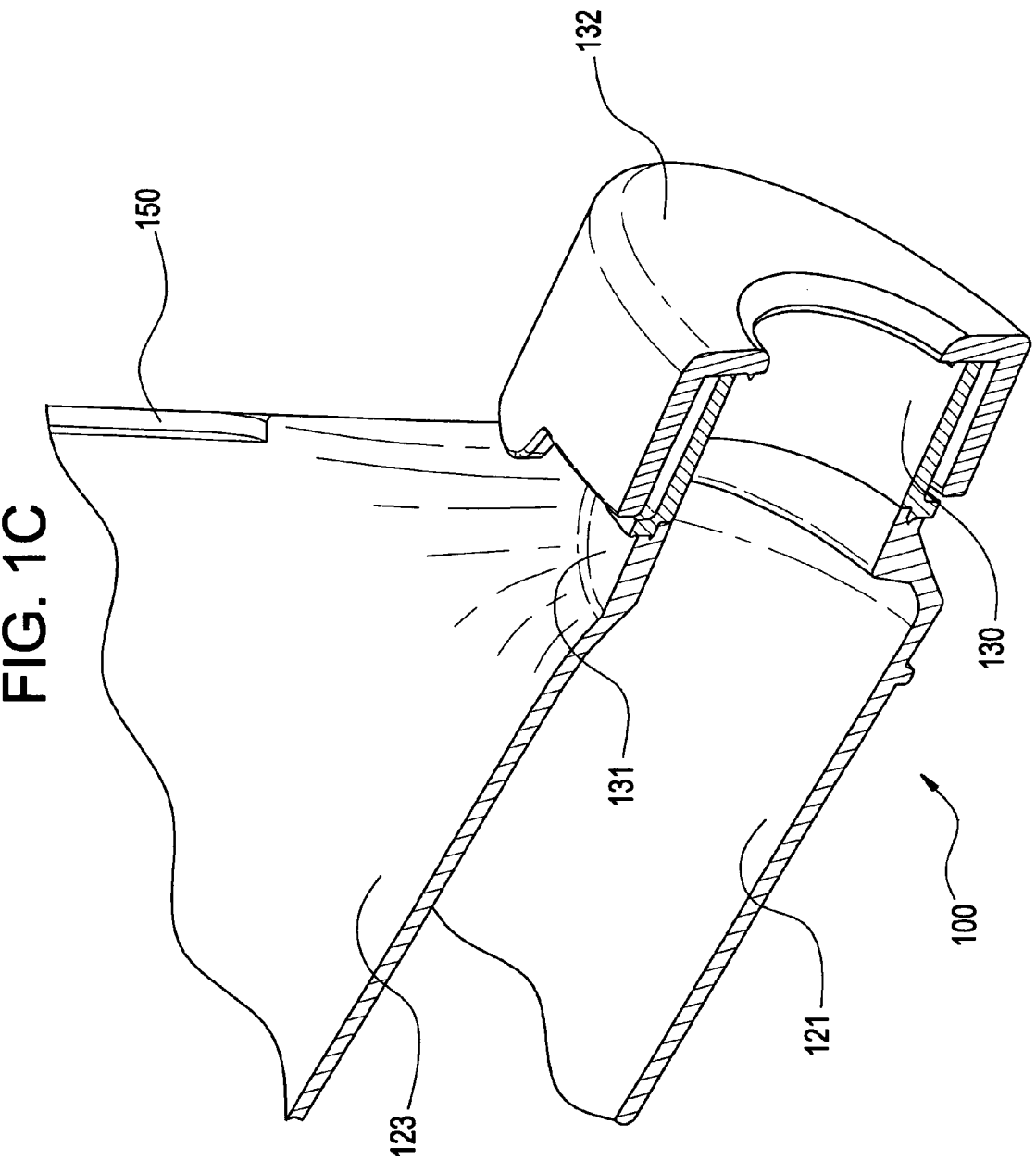

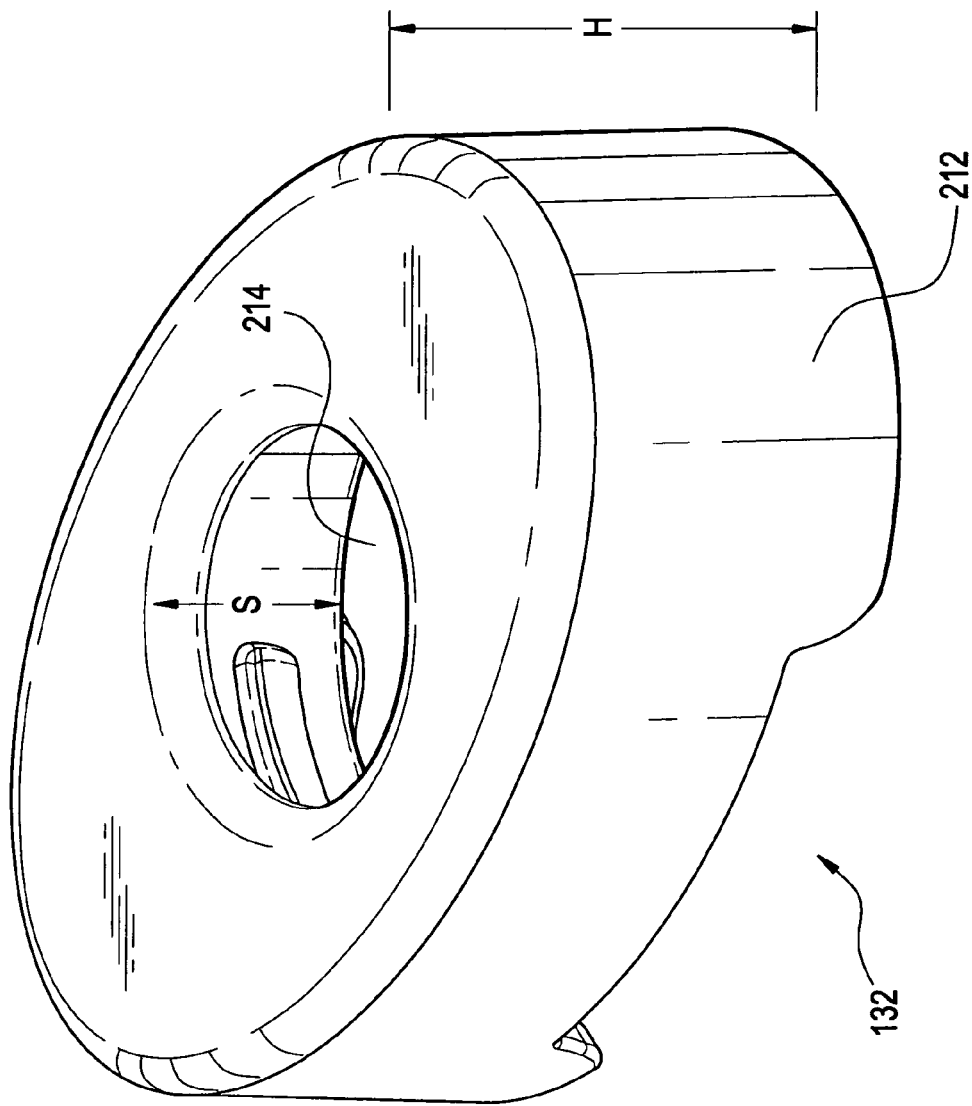

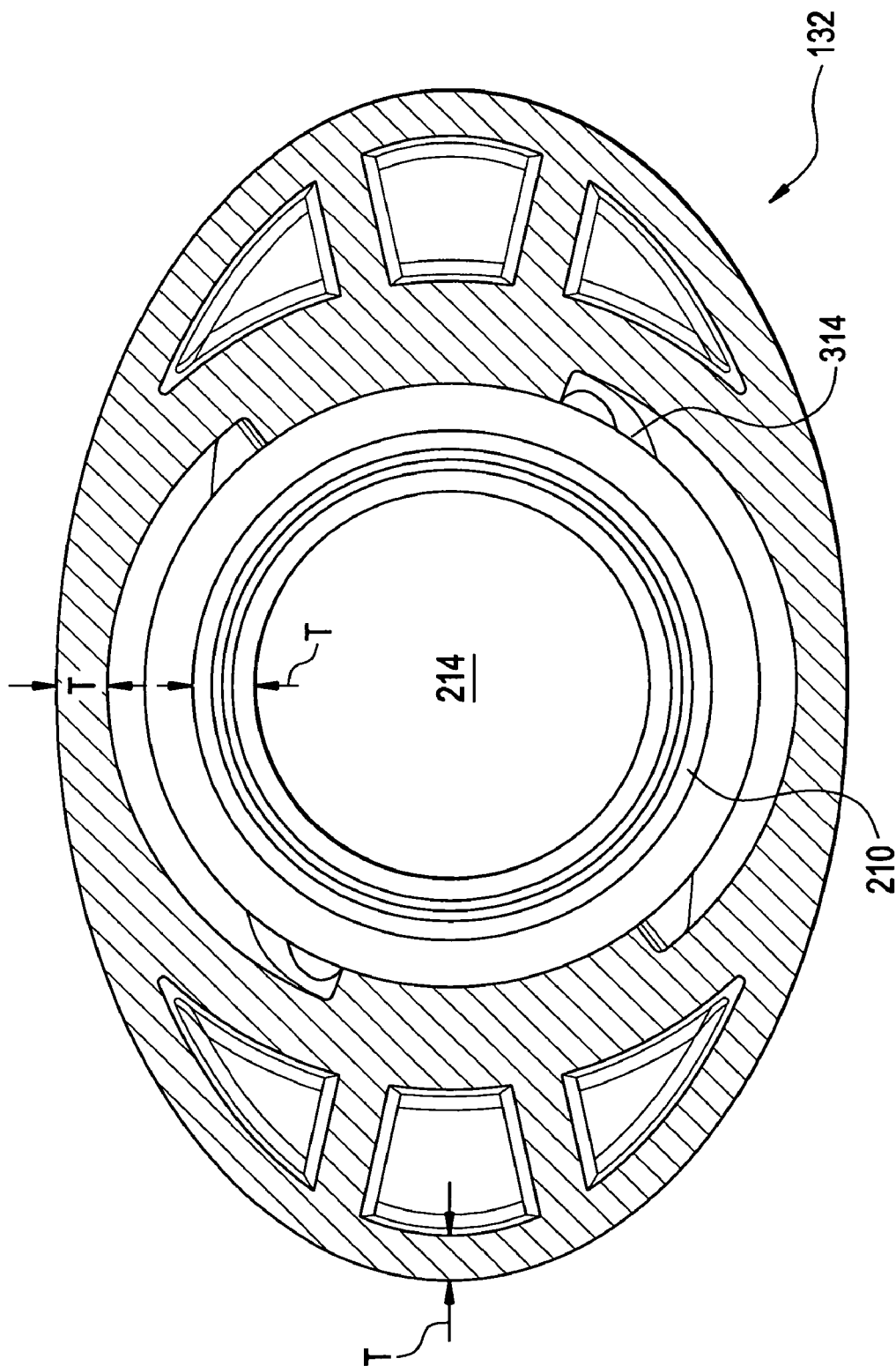

FIG. 3D
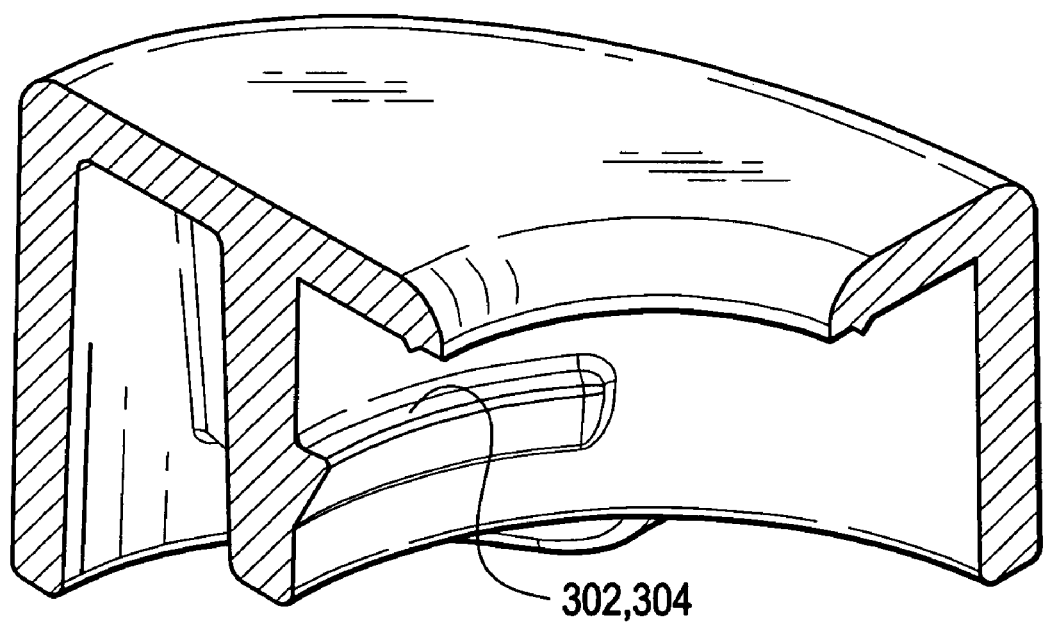
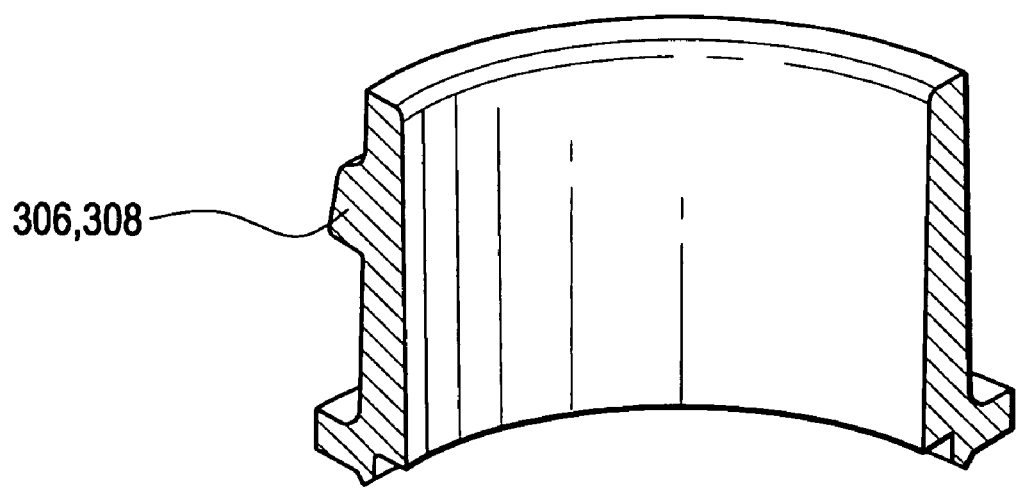

CELL CULTIVATING FLASK

CROSS-REFERENCE TO RELATED APPLICATIONS

This application claims the benefit of U.S. Application Ser. No. 60/662,039 filed on Mar. 14, 2005 and entitled "Cell Cultivating Flask" which is incorporated by reference herein in.

FIELD OF THE INVENTION

The present invention relates generally to the cellular biological field and, in particular, to a cell cultivating flask.

BACKGROUND OF THE INVENTION

In vitro culturing of cells provides material necessary for research in pharmacology, physiology, and toxicology. The environmental conditions created for cultured cells should resemble as closely as possible the conditions experienced by the cells in vivo. One example of a suitable medium for culturing cells is a common laboratory flask such as demonstrated in U.S. Pat. No. 4,770,854 to Lyman. The cells attach to and grow on the bottom wall of the flask, immersed in a suitable sustaining media. The flask is kept in an incubator to maintain it at the proper temperature and atmosphere.

Although most cells will tolerate a hydrogen ion concentration (pH) range of 6.8 to 7.8, the optimal pH for growth of mammalian cells is 7.2 to 7.4. For the optimal pH to be maintained during cell cultivation, the cell culture medium must contain a buffering system.

Frequently, pH is maintained by using a bicarbonate buffering system in the medium, in conjunction with an incubator atmosphere of approximately 5 to 7 percent carbon dioxide by volume. The carbon dioxide reacts with the water to form carbonic acid which in turn interacts with bicarbonate ions in the medium to form a buffering system which maintains the pH near physiological levels. Entry of carbon dioxide from the incubator into the cell culture flask is generally achieved by using a loosely fitting or vented cap or cover so that the small opening remains for the exchange of gas between flask and incubator. Further, flasks have been sold that are made from impact resistant polystyrene plastic which is permeable to water vapor, oxygen and carbon dioxide. However, relying only on the gas exchange through the polystyrene is generally ineffective since the permeability rate is so slow. Further still, flasks have been made having a cell growth surface that is itself an extremely thin (approximately 0.004 inches thick) flexible, gas permeable membrane. While this type of construction allows for gas exchange, the flexibility and thinness of the growth surface makes the growth of a uniform surface difficult and contributes to problems associated with the durability of the flask.

Desirably, many flasks are stacked together in the incubator and a number of cultures are simultaneously grown. Small variations in the growth medium, temperature, and cell variability have a pronounced effect on the progress of the cultures. Consequently, repeated microscopic visual inspections are needed to monitor the growth of the cells. As such, cell culture flasks are typically constructed of optically clear material that will allow such visual inspection.

With the advent of cell-based high throughput applications, fully automated cell culture systems have been the subject of serious development work (see e.g. A Review of Cell Culture Automation, M. E. Kempner, R. A. Felder, JALA Volume 7, No. 2, April/May 2002, pp. 56-62.) These automated systems employ traditional cell culture vessels (i.e. common flasks, roller bottles, and cell culture dishes). These systems invariably require articulated arms to uncap flasks and manipulate them much like the manual operator.

Current molding of standard flasks produces a manufactured flask having unlevel drafts on the exterior surfaces causing the flask to tilt when set on a surface. An improved flask would accommodate these drafts on multiple sides by modifying the flask so that it may sit on a level surface.

There is a need for a cell culture flask having a rigid structure that is capable of providing necessary gas exchange while also accommodating a snap-fit cap for efficient access to the contents of the flask. Furthermore, it is necessary for a neck of the flask to be designed to minimize contamination during use. An improved flask would also be suitable for use in the performance of high throughput assay applications that commonly employ robotic manipulation.

SUMMARY OF THE INVENTION

According to an illustrative embodiment of the present invention, a flask for the efficient culturing of cells is disclosed. The illustrative flask includes a unitary body including a bottom tray defining a cell growth area and a top plate, connected by side walls and end walls. The body of the flask itself can have at least one breathable membrane or film disposed therein. This membrane or film is permeable enough to prevent pressure differential between the flask interior and the external environment. For the addition and removal of media, the flask can be equipped with a septum seal accessible opening or aperture either integrated within the body of the flask itself, or as a part of a cap. The body of the flask has a low profile smaller than about 1 inch but can be of any dimension. The lower profile allows for more efficient use of space, especially when plates are stacked. Any number of features (e.g. standing ribs), can be molded onto the exterior of the flask to allow the flask to be positioned vertically or horizontally while accessing the interior surfaces of the flask. A preferred embodiment of this invention includes two sets of standing ribs on perpendicular sides.

Another improvement over traditional cell cultivating flasks is at least one truncated corner neck disposed therein. Ascending and descending drafts from the bottom and top molded parts, respectively, prevent fluid from being trapped in the corners. Furthermore, the ascending draft provides clearance on the top surface for a cap to be placed without interfering with flasks stacked above and below.

In addition, the neck is canted at an angle and can be hydrophobic to prevent fluid from entering or contaminating the neck area. The canted neck enhances access by way of pipette, scraper, or canulla to the internal contents of the flask. Moreover, the neck of the flask preferably has a protuberance to help secure a snap-fit cap; the protuberance mates with a corresponding feature on the cap. In order to minimize contamination, the snap-fit cap is preferably designed with an elevated skirt so that the cap can be set on a flat surface without the edge of the inner mating surface touching the surface. In addition, the flask of the present invention is shaped and configured to enable robotic access to the flask interior without requiring cumbersome robotic arm manipulation.

BRIEF DESCRIPTION OF THE DRAWINGS

The invention is best understood from the following detailed description when read with the accompanying drawing figures. It is emphasized that the various features are not necessarily drawn to scale. In fact, the dimensions may be arbitrarily increased or decreased for clarity of discussion.

FIG. 1B is an exploded view of an illustrative embodiment of the present invention.

FIG. 1C is a partial cross-sectional view of the flask shown in FIG. 1A.

FIG. 2A is a perspective view of an illustrative embodiment of the preferred snap-fit cap.

FIG. 2B is an end view of an illustrative embodiment of the preferred snap-fit cap.

FIG. 3D is a partial cross-sectional exploded view of a preferred snap-fit cap and neck.

DETAILED DESCRIPTION

Figure 1A:
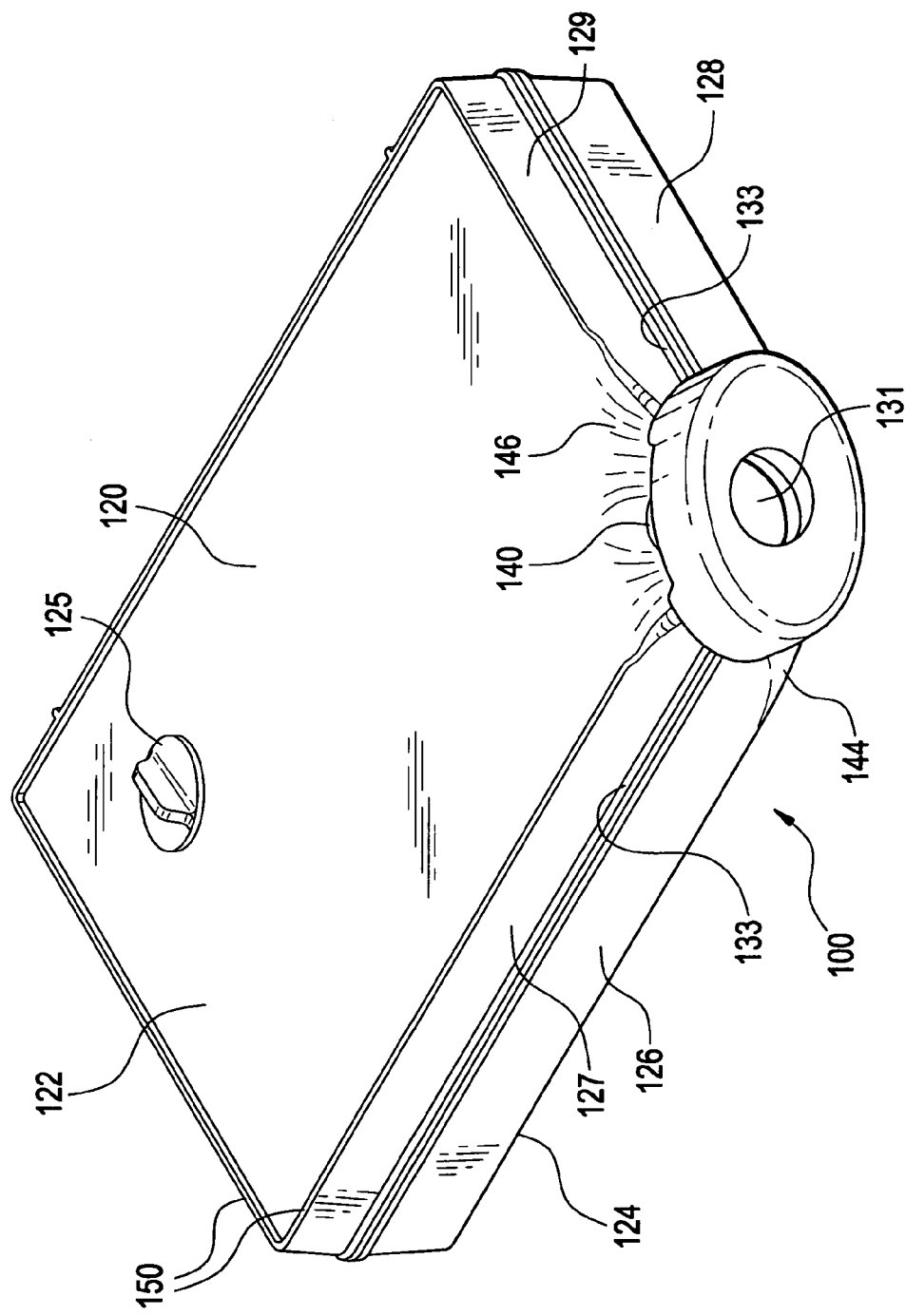
FIG. 1A is a perspective view of an illustrative embodiment of the flask of the present invention.

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Turning to FIGS. 1A, 1B, 1C, and 1D, a flask 100 of the present invention is shown. The flask body 120 comprises a top plate 122 and a bottom tray 124 defining a cell growth surface connected by sidewalls 126, 127 and end walls 128, 129. One embodiment of the present invention can include a vent 125 (FIG. 1E) disposed within the top plate of the flask. The vent 125 may protrude slightly from the surface of the top plate 122 and may be shaped to receive a gas permeable membrane material that provides gaseous communication with the external environment. A necked opening 131 covered by a snap-fit cap 132 is located within a notched/truncated corner 140 of the flask 100. As will be discussed in more detail below, the cap arrangement is preferably arranged such that the cap 132 may protrude only slightly from the rectangular footprint of the flask. The rectangular footprint is the general length by width dimension occupied by the flask when the flask is placed on a surface such that the bottom tray contacts the surface and the top plate faces upwards as demonstrated in FIGS. 1A and 1B. A raised rim 150 may be located on the surface of the top plate serving as a standoff rim 150 intended to contact the bottom tray of an identical flask that is stacked on top the flask 100. Once stacked, the standoff rim 150 allows an air gap between stacked flasks, which is important to allow gas exchange through the vent. Other alternatives for standoffs include raised corners, posts, ledges, or any other feature that will allow spacing between successively stacked flasks. Further, the bottom plate preferably is molded with a rim around the periphery that will engage with the standoff rim from the immediately adjacent flask so as to ensure lateral stability of the stacked flasks.

For polystyrene, the thickness of the bottom tray is preferably greater than 0.5 mm in thickness and more preferably greater than 1 mm. This thickness ensures that the flask bottom be flat, which in use provides a durable surface that will readily attach a uniform cell layer. Although not required, for optical clarity, it is advantageous to maintain a thickness of no greater than 2 mm. The flask 100 may be made by any number of acceptable manufacturing methods well known to those of skill in the art. In a preferred method, the flask is assembled from a collection of separately injection molded parts. Although any polymer suitable for molding and commonly utilized in the manufacture of laboratory ware may be used, polystyrene is preferred. As shown in FIG. 1B, separately molded parts may be formed from different polymers, but are preferably the same material. The bottom tray 124 is a substantially rigid piece having a thickness sufficient to provide stability and rigidity. It is molded such that the sidewalls 126 and end walls 128 are molded together integrally with the bottom tray. This allows for the truncated corner feature 140 of the bottom tray and one-half of the neck portion 131 to be formed.

Similarly, the top plate preferably is molded such that the sidewalls 127 and end walls 129 are molded together integrally to include a truncated corner 140 of the flask. In such a way, a truncated corner 140 may be molded along with a portion of the canted neck. As such, when the bottom tray 124 is aligned with and joined to the top plate 122 (FIG. 1A), a truncated corner 140 in combination with the canted neck becomes fully evident. The top plate 122 and bottom tray 124 are preferably joined by an adhesive bond along the seam 133, ultrasonically welded, or scan welded. Preferably, scan welding equipment is utilized in a partially or fully automated assembly system. The top plate and tray are properly aligned while a scan weld is made along the outer periphery of the joint.

Though the truncated corner of the flask may integrally incorporate the neck of the flask into the molded piece, a preferred embodiment of the present invention incorporates a separate neck 130 for receiving a snap-fit cap 132. A vent 125 can also be molded with a locating structure of any shape and orientation that extends from an inner surface of the top plate 122 and that will properly nest a membrane on the interior portion of the vent structure. The membrane and vent combination allow for the free and instantaneous exchange of gases between the interior of the flask and the external environment and may take any size or shape.

Draft features on the bottom and top surfaces may be located along any edge of the flask so long as the necked opening in combination with the neck itself is canted. A canted neck feature 140 in combination with ascending 144 and descending 146 draft features on bottom and top molded parts, respectively, prevent fluid from being trapped in the corner. In fact, a canted neck allows greater access by pipette, scraper or canulla. Furthermore, the ascending 144 and descending 146 drafts provide clearance for a cap to be placed without interfering with another flask when the flasks are stacked. A preferred embodiment of the invention incorporates the neck into the corner 140 to allow for more cell culture surface area, since the neck and shoulders use less of the footprint area. As a result, access to the cell culture surface with pipettes or cell scrapers is not sacrificed. Due to the preferred corner location of the neck and cap, for instance, a 100 cm² version of the flask of this invention has a similar overall footprint as a standard 75 cm² flask.

Figure 1D:
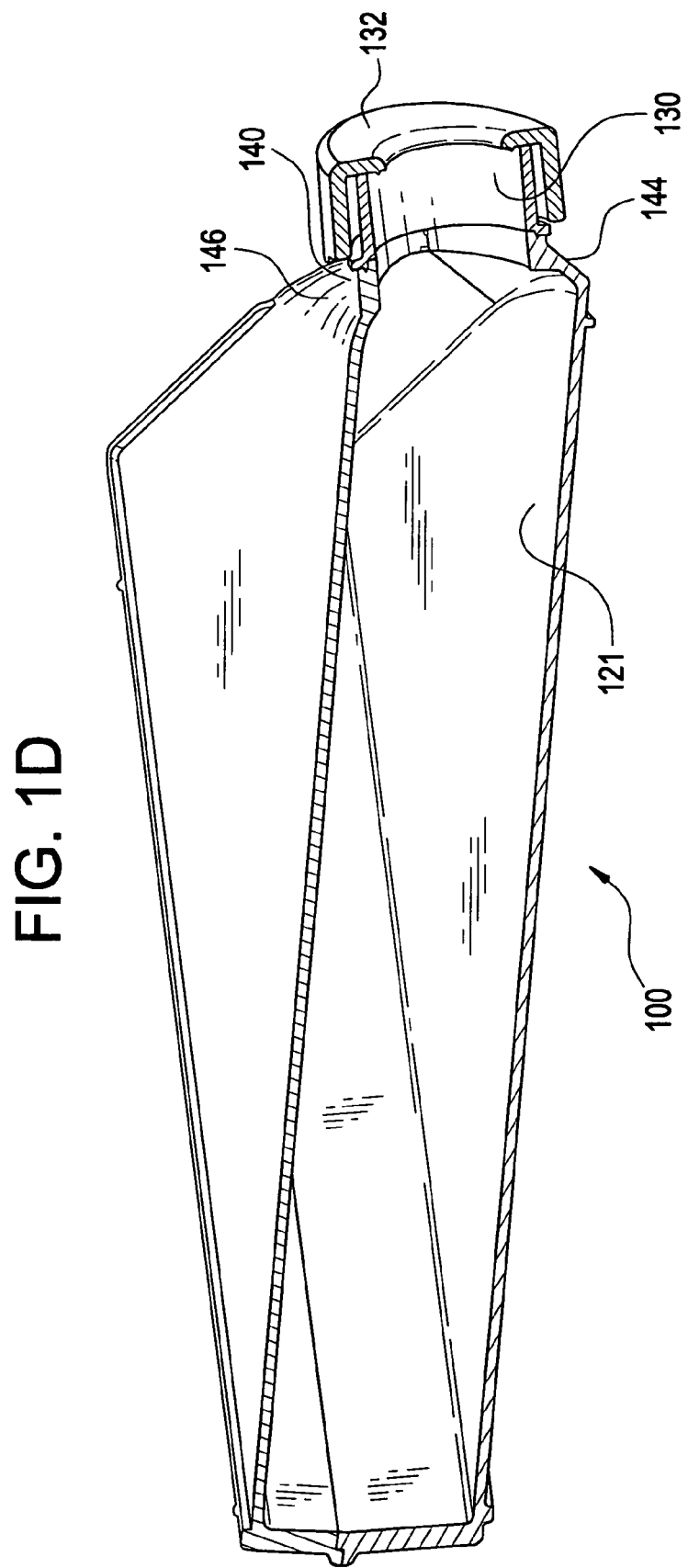
FIG. 1D is an interior cross-sectional view of an illustrative embodiment of the present invention.
Figure 1E:
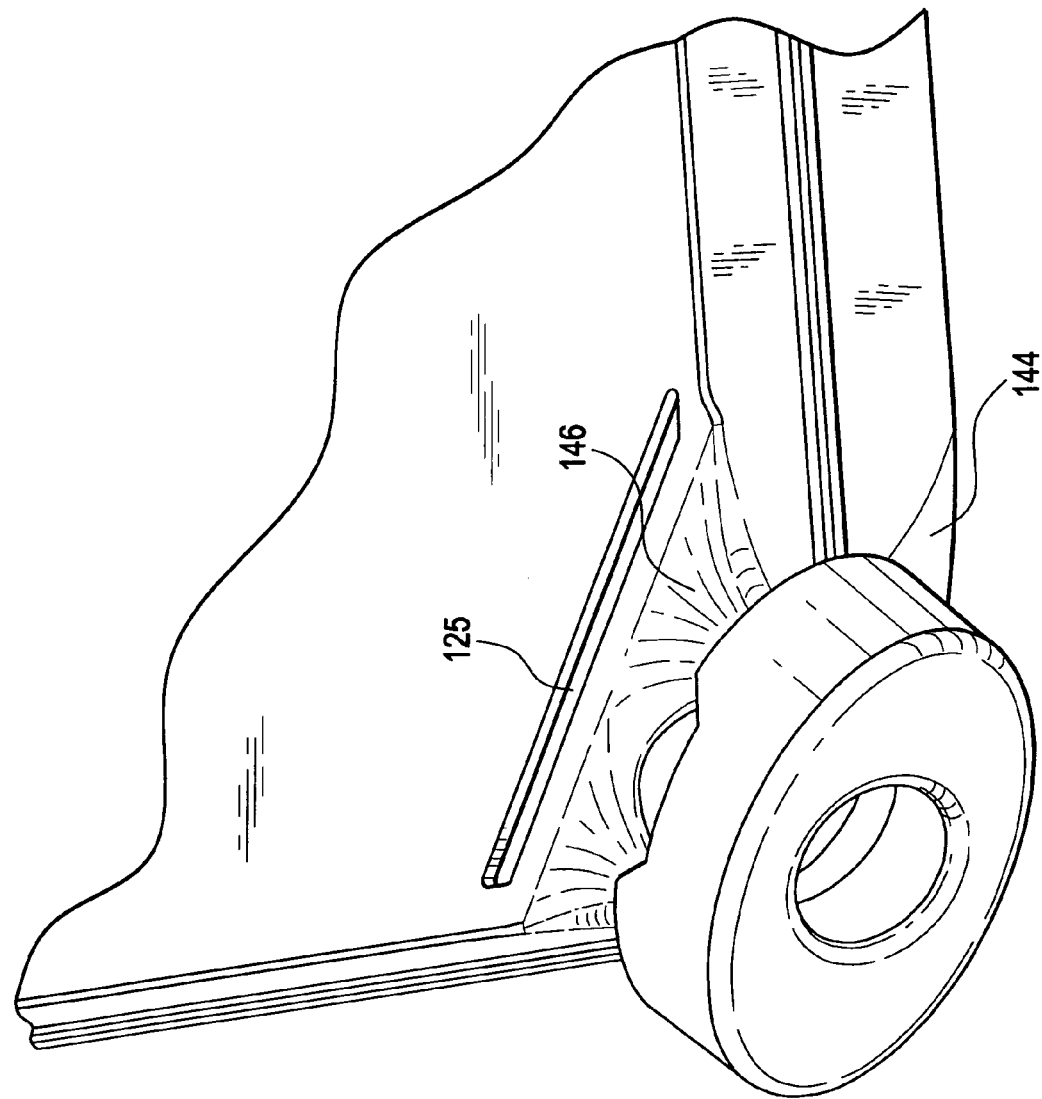
FIG. 1E is a partial perspective view of an illustrative embodiment of the flask having a vent located near the truncated corner, neck and snap-fit cap.

Although the truncated corner having a neck and cap located in the center of one side of the flask may integrally incorporate the entire neck of the flask into the molded piece, a preferred embodiment (FIG. 1B) of the present invention incorporates a separate neck portion 130 for receiving a snap-fit cap 132. One embodiment of the present invention may incorporate a neck 130 having parallel, symmetric sides in a cylindrical shape. An alternative embodiment flares the side surfaces of the neck, from mouth to neck opening, so that an increasing diameter accommodates the exterior draft surfaces 144 and 146 (FIG. 1D). The draft angles of the surfaces, in turn, facilitate fluid from being trapped in the corner. Shown in FIG. 1C is a partial cross-sectional view of the flask shown in FIG. 1A.

The separate neck is bonded to the neck opening 131 in the truncated corner 140 by any number of methods including but not limited to solvent bonding, ultrasonic welding, or heat welding. Heat welding is preferred to establish a hermetic seal.

Figure 3A:
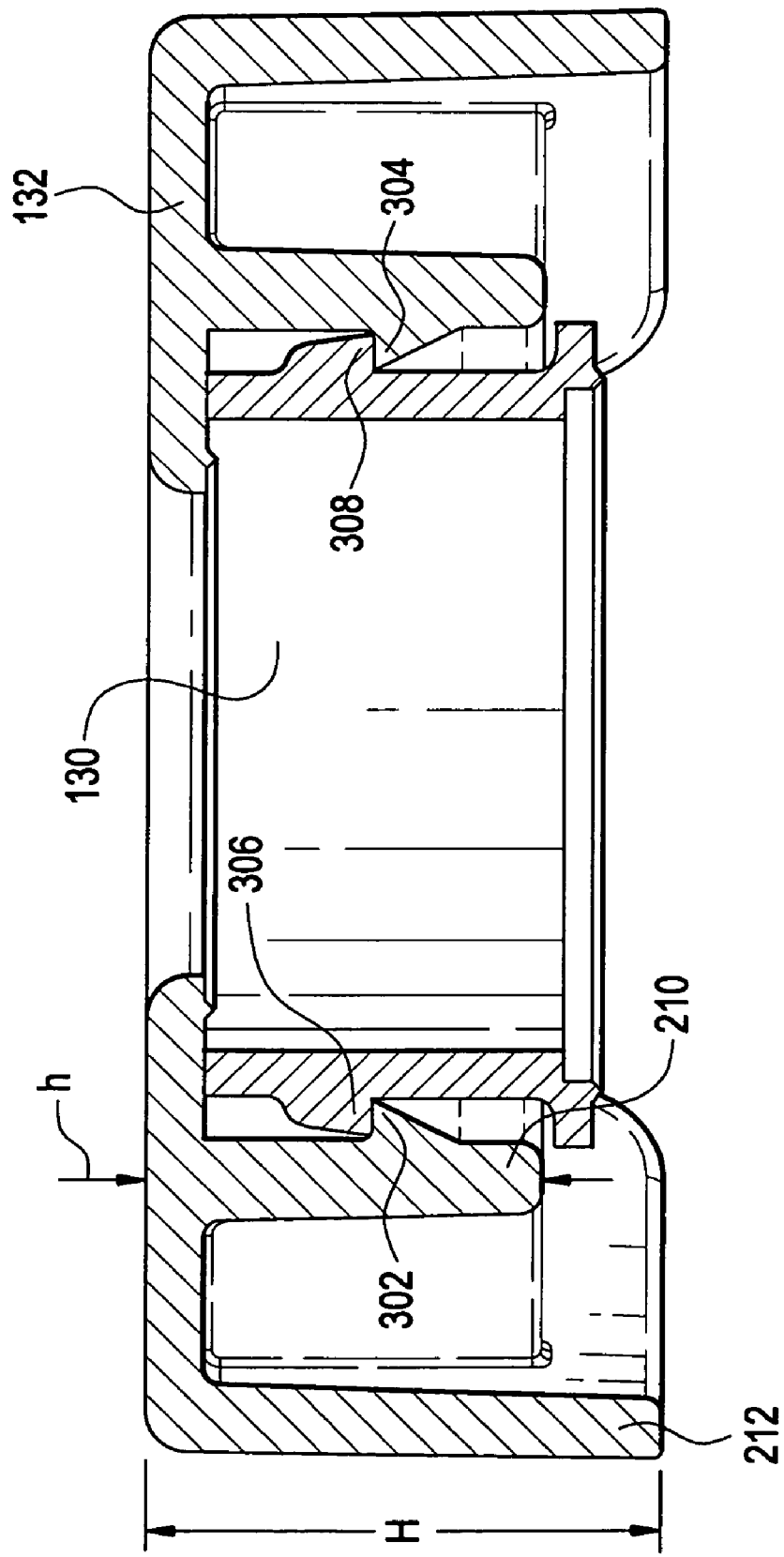
FIG. 3A is a partial cross-sectional side view of a preferred snap-fit cap and neck in closed position, the interlock having undercuts.
Figure 3B:
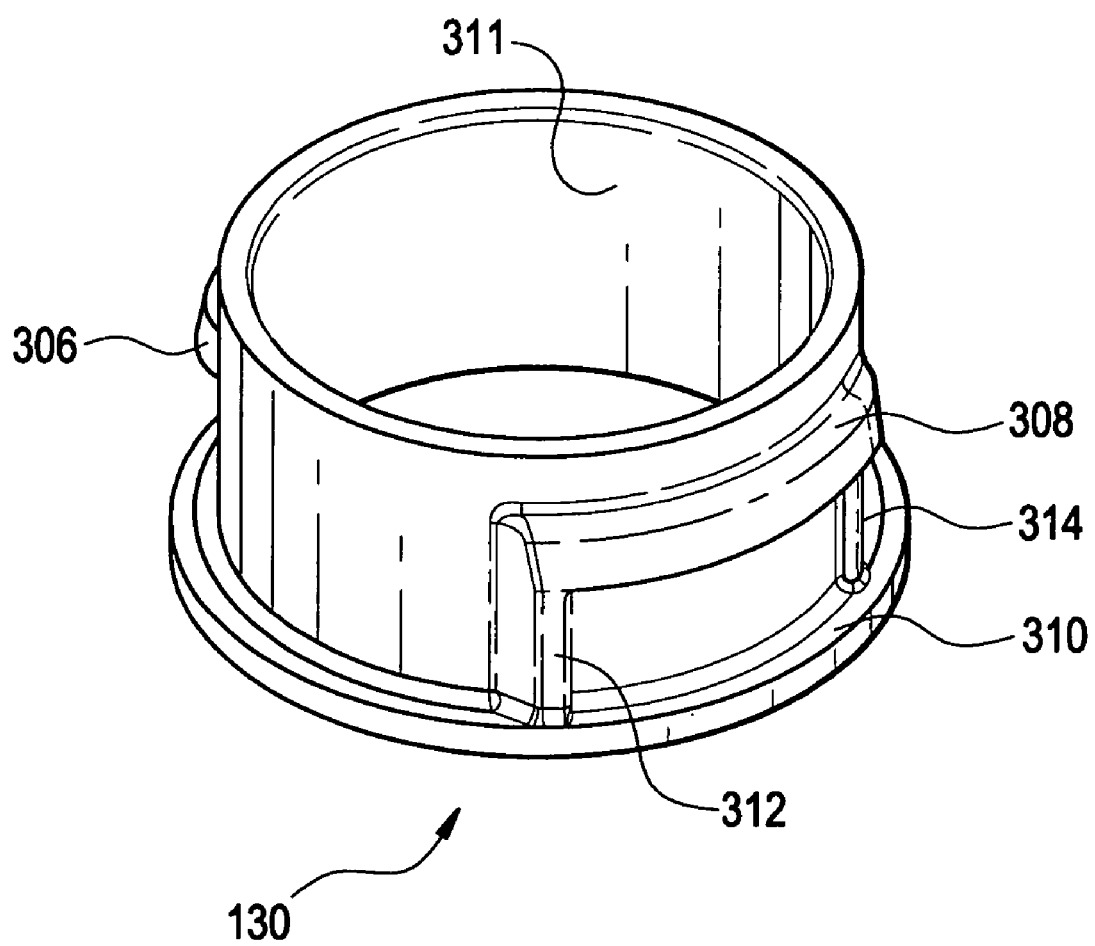
FIG. 3B is a perspective view of an illustrative embodiment of the preferred separate neck with snap-fit features.
Figure 3C:
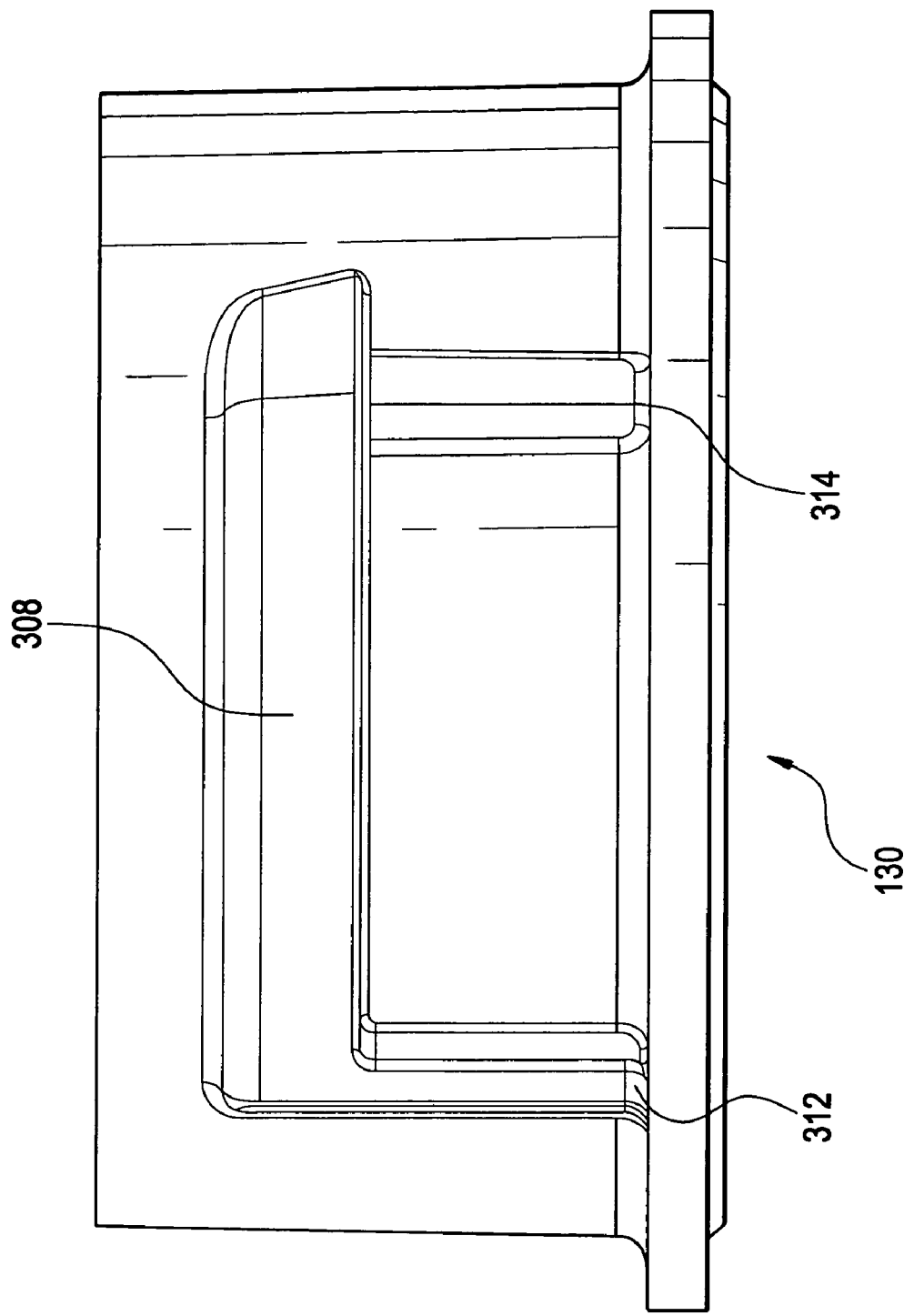
FIG. 3C is a side view of a preferred separate neck with snap-fit features.

Referring to FIG. 3B, the neck 130 may be of any size or shape and should preferably be capable of blocking the entrance or exit of undesired fluid between the interior of the flask and the external environment. The interior surface 311 of the neck 130 is preferably hydrophobic (non-wetting) neck in order to wick fluids away from the cap area (an area that is typically a contamination concern). As such, it is preferred that the neck 130 of the flask be hydrophobic or made from material that can be made hydrophobic by proper treatment methods. Although other hydrophobic treatments or coatings are acceptable, examples of suitable materials for the separate neck include (but are not limited to): polytetrafluoroethylene (PTFE), polyvinylidene fluoride (PVDF) or compatible fluoropolymer, or polypropylene.

As shown in FIG. 1D, the neck 130 is further described as being canted at an angle and raised from the bottom surface to prevent fluid from getting near the opening. Although a threaded cap may be utilized, the snap-fit of cap 132 ensures easier placement/removal of the cap and actually shortens the necessary neck length required by conventional thread screw caps. A small protuberance 308 (FIG. 3B) on the neck 130 is preferably added to the leading edge of the neck and undercut, further providing an interference 314 that will produce an actual snap feel or sound when the cap is secured into its snap-fit position. The snap-fit design ensures the cap is properly connected to the flask assembly.

A design of the present invention illustrates the preferred snap-fit cap (FIGS. 2A and 2B) of the cell cultivating flask to have an oval footprint. The oval design preferably has a minor axis less than or equal to the height of the flask. This way the flasks may be stacked. However, the shape and size of the snap fit cap is not limited to the preferred embodiment; any shape and size may work. The mouth of the neck having flare out walls into the flask can be accommodated by a snap-fit cap also. Further, the preferred snap-fit cap has a cylindrical recess 210 inscribed on the underside of the oval; this is the mating feature for the neck. The inscribed cylindrical recess 210 has a wall thickness preferably equal to that of the exterior oval. In the same continuum, any cap footprint or wall dimensions, shapes or sizes, may be suitable for the snap-fit design. The height of the cylindrical wall 210 is a value less than H (named h) creating a stepped skirt 210. This stepped skirt 210 is designed such that the longer sections 212 of height H do not interfere with the edges of the flask during closure. Further, the longer section 212 contacts a lab bench preventing contamination of the skirt 210. The preferred snap-fit cap also has a circular through-hole 214 that provides an opening for a vent or septum, though any shape through-hole is possible.

The desired snap-fit cap 132 utilizes a maximum ¼ turn (non-thread) snap-fit. FIGS. 3A, 3B, 3C, and 3D illustrate both the cap and neck having two undercut features 302/304 and 306/308, respectively, each that is slightly less than 90° about the circumference. The number of undercuts can vary, but should be evenly spaced. With each additional undercut, the amount of turn will be reduced. Interferences in the cap will line up with the opening of the neck for removal, but the interferences will be enough to hold the cap on when aligned. On the preferred neck, the undercut 308 is bounded on the left edge (for a clockwise turn) by a vertical wall 312 of equal depth. This wall acts as a stop for the cap. A second vertical feature, the interference 314 can be added near the leading edge of the neck undercut (the right side of a clockwise turning cap). This feature should be thick enough to cause a small amount of interference with the cap undercut and should be placed beyond the corresponding arc length of the cap when touching the neck's stop, preferably providing a snap sound or feel once the cap is closed.

Other specialized features can be incorporated into the neck when it is manufactured separately and then assembled to the main body of the flask. For example, the neck may include a flexible joint that would allow for even greater range of access (i.e. when pipetting or scraping cells). If the neck is made in an over-molding process, a band of flexible material can be integrated in its diameter to enable such utility.

Finally, when a snap-fit cap 132 is provided, its quick and convenient placement or removal allows a user to access the opening to the interior contents of the flask by way of a cannula, tip or needle with minimized contamination. It is preferred that a septum seals the access hole. The septum is preferably leak proof, puncturable and capable of resealing once the needle, tip or cannula is removed from the flask, even after multiple punctures. The septum itself may take any form well known to those of skill in the art including a slit arrangement useful for blunt needles and as generally described in WO 02/066595, the contents of which are incorporated herein by reference.

In another embodiment the snap-fit cap may be directly fitted to the body of the flask without a neck. In this case, modifications to the body of the flask may include a lip-type feature or protuberance(s) to accept a cap having a mating/connecting feature to enclose the flask contents.

In a preferred embodiment, the present invention has a footprint conforming to industry standard for microplates (5.030+/−0.010 inches by 3.365+/−0.010 inches). For this reason, the neck portion is preferably recessed within the overall rectangular footprint. The advantage of providing a flask with such a footprint is that automated equipment designed specifically for the manipulation of microplates may be utilized with this flask with very little customized modification. Similarly, the height, or the distance between the outer most portion of the bottom tray and the outer portion of the top plate, may conform to microplate standards; the height to be approximately 0.685+/−0.010 inches. Though is advantageous to have a flask with a height of less than about 1½ inches, it is preferred to have a flask having a height of about 1 inch. At any rate, the present invention is not intended to be limited in any way by the aforementioned preferred dimensions and in fact may be constructed to any dimension.

Figure 1F:
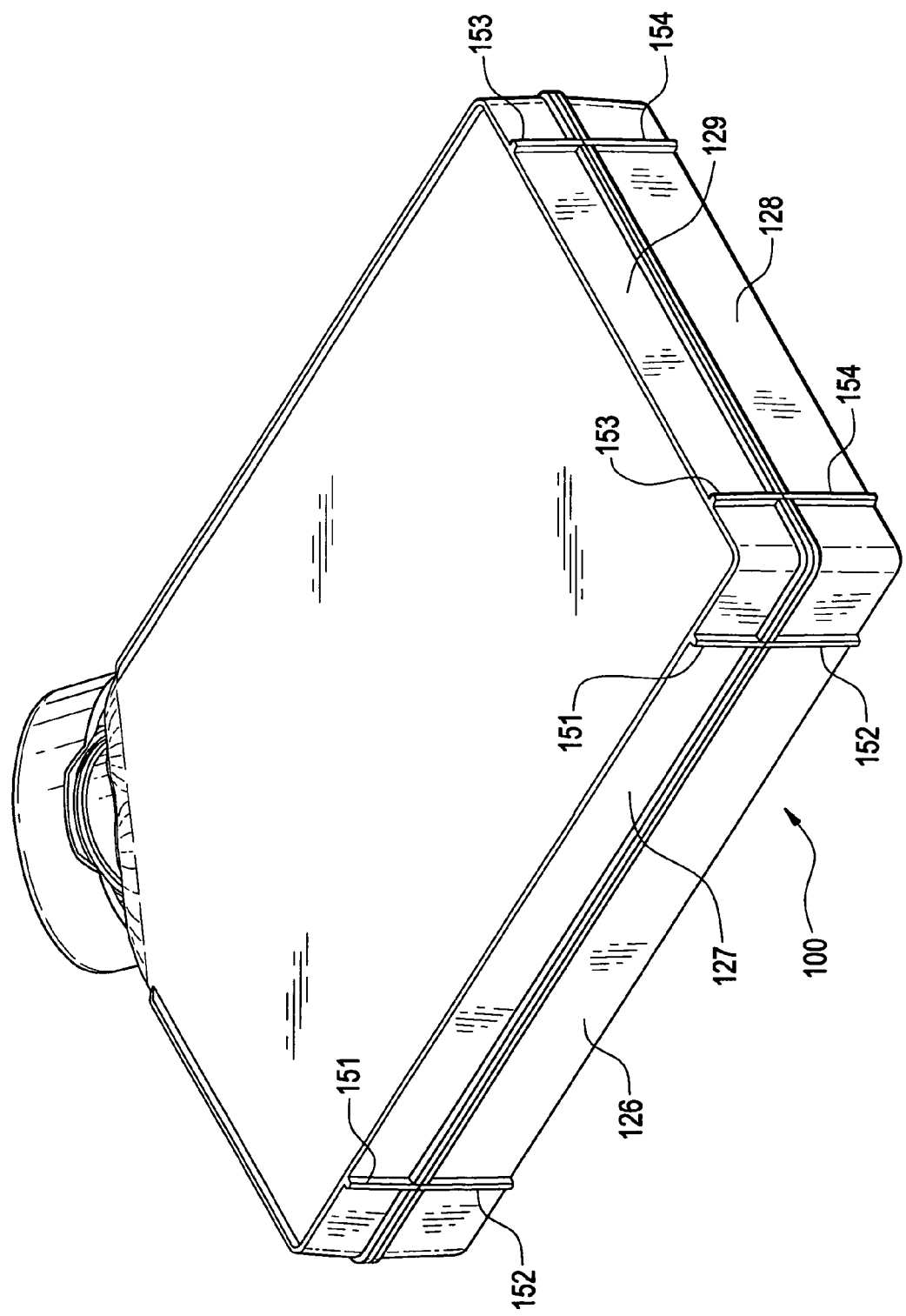
FIG. 1F is another perspective view of an illustrative embodiment of the flask of the present invention having standing ribs on the exterior side walls of two adjacent sides.

In use, the flask of the current invention is employed according to accepted cell growth methods. Cells are introduced to the flask though a neck or through a septum. Along with the cells, media is introduced such that the cells are immersed in the media. The flask is arranged such that the cell containing media covers the cell growth surface of the bottom tray. It is important not to completely fill the flask so as not to cover the membrane/vent combination. This will ensure the free and rapid exchange of gases between flask interior and the external environment. The flask is then placed within an incubator and may be stacked together with similar flasks such that a number of cell cultures are simultaneously grown. The flask is situated such that the bottom tray assumes a horizontal position that will allow it to be completely covered by media. An alternative embodiment of the cell cultivating flask includes a number of features ridged onto the exterior of the flask to allow the flask to be positioned vertically or horizontally while accessing the interior surfaces of the flask. A preferred embodiment of this invention includes two sets of standing ribs 151/153 and 152/154 on perpendicular sides (FIG. 1F) to accommodate the draft from the mold. The standing ribs 151/153 and 152/154 allow the flask to be set level on a surface, without tilt.

Advantageously and in order to enhance cell attachment and growth, the surface of the bottom tray is treated to make it hydrophilic. Treatment may be accomplished by any number of methods known in the art which include plasma discharge, corona discharge, gas plasma discharge, ion bombardment, ionizing radiation, and high intensity UV light. Although cell attachment is typically targeted for only one surface (the bottom tray), other parts of the flask may be treated so as to enable cell growth on all surfaces of the flask interior.

Cell growth is monitored from time to time by microscopic inspection through the bottom tray. During the cell growth process, it may become necessary to extract the exhausted media and insert fresh media. As previously described, media replacement may be achieved through insertion of a cannula, for example, through the septum. Alternatively, the media may be replaced by removing the cap, in embodiments that offer this option. Once the cells are ready for harvesting, a chemical additive such as trypsin is added to the flask through the septum. The trypsin has the effect of releasing the cells from the flask walls. The cells are then harvested from the flask.

The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

We claim:

1. A flask for the growth of cells comprising:
   a flask body serving as a cell culture chamber defined by a bottom tray having a rigid surface and a top plate, the bottom tray and top plate connected by side walls and end walls,
   the flask body having a substantially rectangular shape,
   a neck canted at an angle connected to and extending from the flask body, the neck having an opening providing access to the cell culture chamber,
   a snap-cap for covering said neck opening,
   a truncated corner from said substantially rectangular shape,
   wherein the neck comprises a flexible joint,
   whereby the neck and cap extend from the truncated corner such that the neck and snap-fit cap remain within the substantially rectangular footprint.

* * * * *